United States Patent [19]

Hoshino et al.

[11] Patent Number: 5,331,167
[45] Date of Patent: Jul. 19, 1994

[54] METHOD AND APPARATUS FOR INSPECTING HEAT-RESISTANT MULTILAYER CONTAINERS MADE OF SYNTHETIC RESIN

[75] Inventors: Masaru Hoshino; Tsutoo Yamada, both of Tokyo, Japan

[73] Assignee: Dai Nippon Insatsu Kabushiki Kaisha, Tokyo, Japan

[21] Appl. No.: 582,833

[22] PCT Filed: Feb. 6, 1989

[86] PCT No.: PCT/JP89/00118
§ 371 Date: Dec. 3, 1990
§ 102(e) Date: Dec. 3, 1990

[87] PCT Pub. No.: WO90/08951
PCT Pub. Date: Aug. 9, 1990

[51] Int. Cl.⁵ ............................................. G01N 21/90
[52] U.S. Cl. ................................ 250/372; 250/223 B; 209/578
[58] Field of Search ............. 250/372, 341, 223 B; 209/578, 577, 588

[56] References Cited

U.S. PATENT DOCUMENTS

| | | | |
|---|---|---|---|
| 4,391,373 | 7/1983 | Wiggens | 250/223 B |
| 4,650,326 | 3/1987 | Nagamine et al. | 250/223 B |
| 4,701,612 | 10/1987 | Sturgill | 250/223 B |
| 4,731,649 | 3/1988 | Chang et al. | 250/223 B |
| 4,807,995 | 2/1989 | Dassler | 250/223 B |
| 4,831,250 | 5/1989 | Fukuchi et al. | 250/223 B |
| 4,919,534 | 4/1990 | Reed | 250/226 |
| 4,945,228 | 7/1990 | Juvinall et al. | 250/223 B |
| 5,008,533 | 4/1991 | Lee, Jr. | 250/223 B |

FOREIGN PATENT DOCUMENTS

| | | | |
|---|---|---|---|
| 63-142242 | 6/1988 | Japan | 250/372 |
| 63-154951 | 6/1988 | Japan | 250/372 |
| 63-175750 | 7/1988 | Japan . | |
| 63-193047 | 8/1988 | Japan . | |

Primary Examiner—Carolyn E. Fields
Assistant Examiner—Drew A. Dunn
Attorney, Agent, or Firm—Wegner, Cantor, Mueller & Player

[57] ABSTRACT

The present invention relates to a method of inspecting a heat-resistant multilayer container made of synthetic resin characterized by projecting a light to an upper end portion of a mouth portion of a heat-resistant multilayer container manufactured by the blow formation of a parison made of a main resin and a heat-resistant resin, receiving light passing the upper end portion of the mouth portion, extracting and detecting a light having a specific wavelength, outputting the light as an electrical signal and evaluating the quality of the heat-resistant multilayer container in accordance with the outputted signal value, relates to an apparatus for inspecting a heat-resistant multilayer container made of synthetic resin characterized by comprising a lighting device (121, 221) for emitting a light, a light projecting device (122, 222) connected to the lighting device (121, 221) and adapted to transfer and project the light to an upper end portion of the mouth portion, a light receiving device (124, 224) located opposingly to the light projecting device (122, 222) and adapted to receive and transfer the light passing the upper end portion of the mouth portion of the container, a sensor (129, 229) for extracting and detecting a light transmitted from the light receiving device (124, 224), and a signal processing circuit means for processing an electric signal from the sensor (129, 229).

14 Claims, 16 Drawing Sheets

000
METHOD AND APPARATUS FOR INSPECTING HEAT-RESISTANT MULTILAYER CONTAINERS MADE OF SYNTHETIC RESIN

TECHNICAL FIELD

The present invention relates to a method of inspecting a heat-resistant multilayer container made of synthetic resin, capable of evaluating the quality of a product of a heat-resistant multilayer container on the basis of a non-destructive technology and to an apparatus to be utilized for the method.

BACKGROUND ART

Marketing of containers made of synthetic resin, particularly of PET (Polyethylene Terephthalate), has been widely developed mainly regarding large sized containers for soft drinks. Recently, usage of a heat resistant container has been required and, hence, much study and development has been carried out.

Synthetic resin containers of the heat-resistant multilayer type are generally composed of a mouth portion with which a lid is screw engaged, and a shell portion continuous to the lower end of the mouth portion. Such containers are manufactured by forming a parison formed of a main resin and a heat-resistant resin and forming a shell portion by holding a mouth portion of the parison and by performing a drawing blow process.

The formation of the heat resistant container involves such problems as degradation of the heat resistant deformability, chemical resistance and strength of the mouth portion because the mouth portion is not drawn and maintained as it is injected. In order to obviate these problems, conventional art provides such methods as (a) a method in which the mouth portion is heat crystallized, (b) a method in which the mouth portion is formed by two-color formation of the heat-resistant resin and (c) a method in which the mouth portion is formed by preliminarily forming an outer periphery of the mouth portion with the heat-resistant resin and carrying out insertion formation in the preliminarily formed product.

However, the mouth portion formed by the method (a) involves faults such that diameters of a screw thread and a screw root thread of the mouth portion as well as the size thereof are not stably formed because of shape deformation during the heat crystallization process of the mouth portion, the sealing performance thereof is degraded because of the deformation of a top surface of a seal portion, and this method also is not applicable in a case where a totally transparent container is required, because of the opacity due to the crystallization. Furthermore, a crystallizing process is additionally needed, resulting in less productivity of products and an increased cost.

The mouth portion formed by the method (b) has an insufficient layer-to-layer adhesive strength between the main resin and the heat-resistant resin and, in addition, requires a plurality of molding devices for the manufacturing thereof, involving complicated processes and, hence, resulting in cost respectively.

The mouth portion formed by the method (c) has also insufficient layer-to-layer adhesive strength between the main resin and the heat-resistant resin and also requires a plurality of molding devices. An insert device is further needed, thus also involving complicated processes and cost respectively.

There has been proposed a further method for eliminating the defects described above in which the main and heat resistant resins are co-injected from the lower portion to thereby form a parison and the parison is thereafter subjected to drawing blow formation to form a heat-resistant multilayer container. In such a parison formation method, it is required to utilize a hot runner for uniformly co-injecting the molten resin of the main and heat-resistant resins in accordance with the predetermined timing and injection quantity. The applicant of the present invention has developed a co-injection molding machine provided with a hot runner in which a hot runner portion, except a hot-runner branching point and a portion near that point, is composed of a pair of molten resin flow passages extending mutually closely and having the same cross sections and there is provided an area which combines two resin flows to the branching point (Japanese Patent Laid-open Publication No. 61-252977).

It is required to evaluate the performance and the quality of the heat resistant containers manufactured by the methods described above. The evaluation for the good performance and quality is based on a standard such as the heat-resistant resin is concentrated in the mouth portion of the heat-resistant multilayer container.

The conventional discrimination includes a visual checking method, but this method is not suitable for respectively in the case of the main and heat resistant resins both having the same color or both being transparent. It may be possible to evaluate the performance and the quality by a non-destructive technique based on a sampling method, but this method lacks reliability because this method involves unstable factors in the manufacturing process and, hence, fears of causing unexpected faults when compared with single-layered containers.

DISCLOSURE OF THE INVENTION

The first object of the present invention is to provide a method and apparatus for inspecting in a non-destructive manner, as to whether or not the heat-resistant resin layer exists uniformly throughout a heat-resistant multilayer container.

The second object of the present invention is to provide method and apparatus for inspecting in a non-destructive manner the flow condition of the heat-resistant resin layer at a mouth portion of a heat-resistant multilayer container.

The third object of the present invention is to provide a container rotating mechanism for stably rotating the heat-resistant multilayer container while accurately inspecting the container and maintaining a perpendicularly accurate attitude of the container for the entire peripheral inspection of the container.

The fourth object of the present invention is to provide a transfer device for continuously transferring heat-resistant multilayer containers for continuous, multiple inspection of the containers.

(1) The first characteristic feature of the present invention resides in an inspection method for a heat-resistant multilayer container made of synthetic resin, the method being characterized by projecting light to an upper end portion of a mouth portion of a heat-resistant multilayer container formed by blow forming a parison made of a main resin and a heat-resistant resin, receiving light passing the upper end portion of the mouth portion, extracting and detecting a light having a specific wavelength, than outputting the light as an electric signal and respectively the quality of the heat-resistant multilayer container in accordance with the output signal value.

(2) The second characteristic feature of the present invention resides in an inspection method for a heat-resistant multilayer container made of synthetic resin, the method being characterized by projecting light to an upper end portion of a mouth portion and a lower thread portion of the mouth portion of a heat-resistant multilayer container formed by blow forming a parison made of a main resin and a heat-resistant resin, receiving light passing the upper end portion and the lower screw thread portion of the mouth portion, extracting and detecting a light having a specific wave length, then outputting the light as an electric signal and respectively the quality of the heat-resistant multilayer container in accordance with the output signal value.

(3) The third characteristic feature of the present invention resides in an inspection apparatus to be utilized for carrying out the above-mentioned inspection method (1) for a heat-resistant multilayer container made of synthetic resin, the apparatus comprising a lighting device for emitting a light, a light projecting device connected to the lighting device and adapted to transfer and project the light to an upper end portion of a mouth portion of a heat resistant multilayer container made of synthetic resin, a light receiving device located opposingly to the light projecting device and adapted to receive and transfer the light passing the upper end portion of the mouth portion of the container, a sensor for extracting and detecting a light transmitted from the light receiving device, and a signal processing circuit means for processing an electric signal from the sensor.

(4) The fourth characteristic feature of the present invention resides in an inspection apparatus to be utilized for carrying out the above-mentioned inspection method (2) for a heat-resistant multilayer container made of synthetic resin, the apparatus comprising a lighting device for emitting a light, a plurality of light projecting devices each connected to the lighting device and adapted to transfer and project the light to an upper end portion and a lower screw thread portion of a mouth portion of a heat-resistant multilayer container made of synthetic resin, a plurality of light receiving devices located opposite the light projecting devices and adapted to receive and transfer the light passing the upper end portion and the lower screw thread portion of the mouth portion of the container, a plurality of sensors for extracting and detecting lights transmitted from the respective light receiving devices, and a plurality of signal processing circuit means for processing electric signals from the respective sensors.

(5) The fifth characteristic feature of the present invention resides in a container rotating mechanism characterized by comprising a pair of freely rotatable rollers and one driving roller which holds a flanged portion of a mouth portion of a container at three portions, a pair of roller support rods which support at one end the rotatable rollers and which can be bilaterally freely opened and closed for embracing the flanged portion of the mouth portion, a mechanism for bilaterally opening and closing the paired roller support rods, and a mechanism for driving the driving roller.

(6) The sixth characteristic feature of the present invention resides in a container transfer device characterized in that a plurality of container rotating mechanisms characterized in the above feature (5) are arranged at a predetermined spacing to each other on the circumference of a rotary disc connected to a take-in conveyer and a take-out conveyer.

BEST MODE FOR CARRYING OUT THE INVENTION

Figure 6:
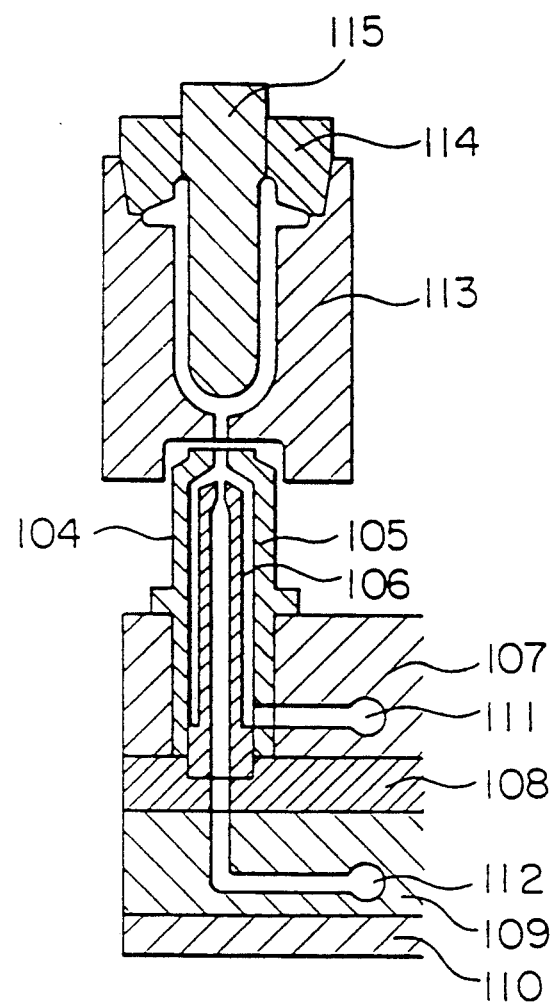
FIG. 6 is a sectional side view of a co-injection molding machine for forming a parison.
Figure 7:
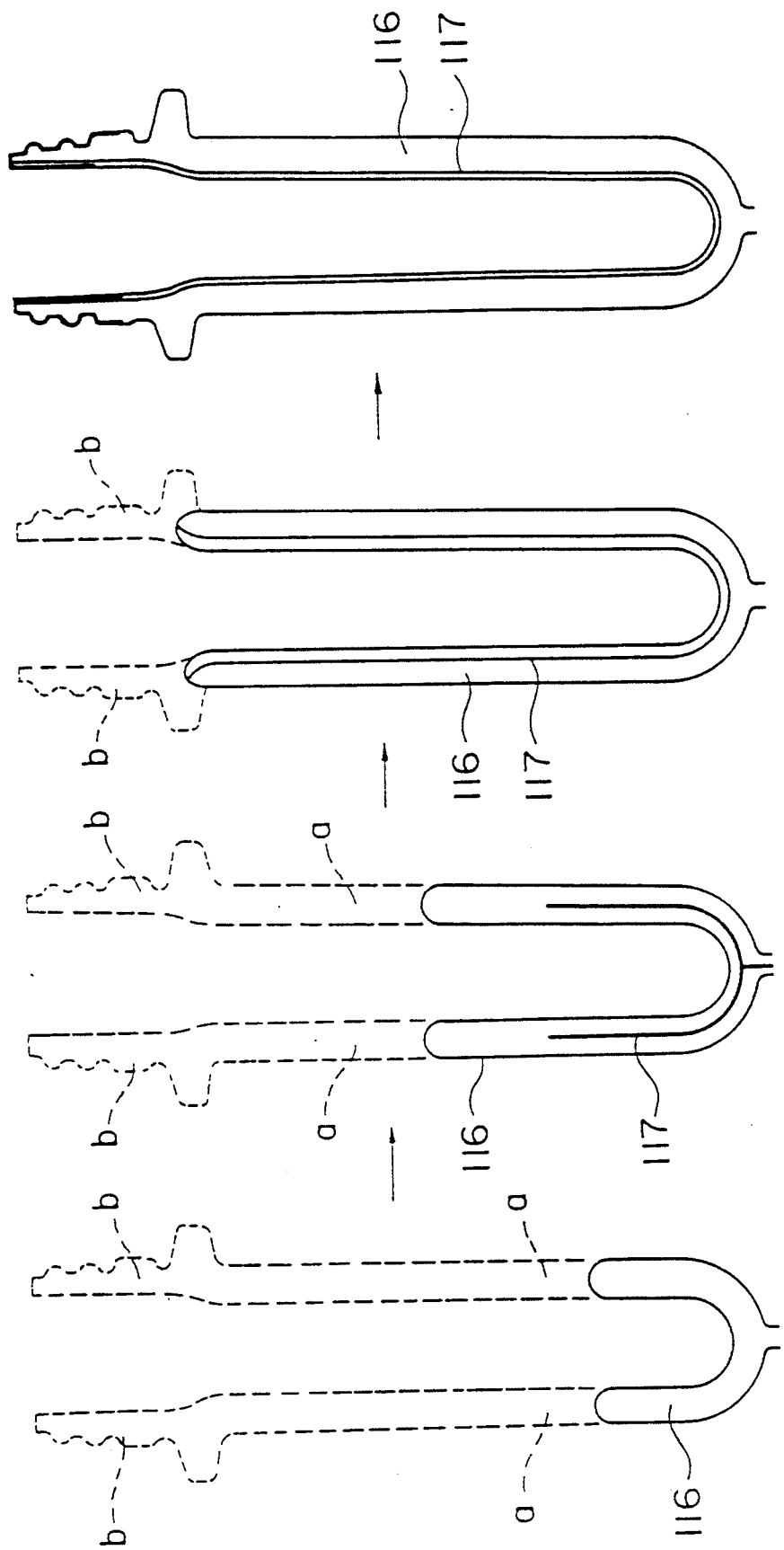
FIGS. 7(A), 7(B), 7(C), and 7(D) are views showing the parison formation processes by the utilization of the coinjection molding machine.
Figure 8:
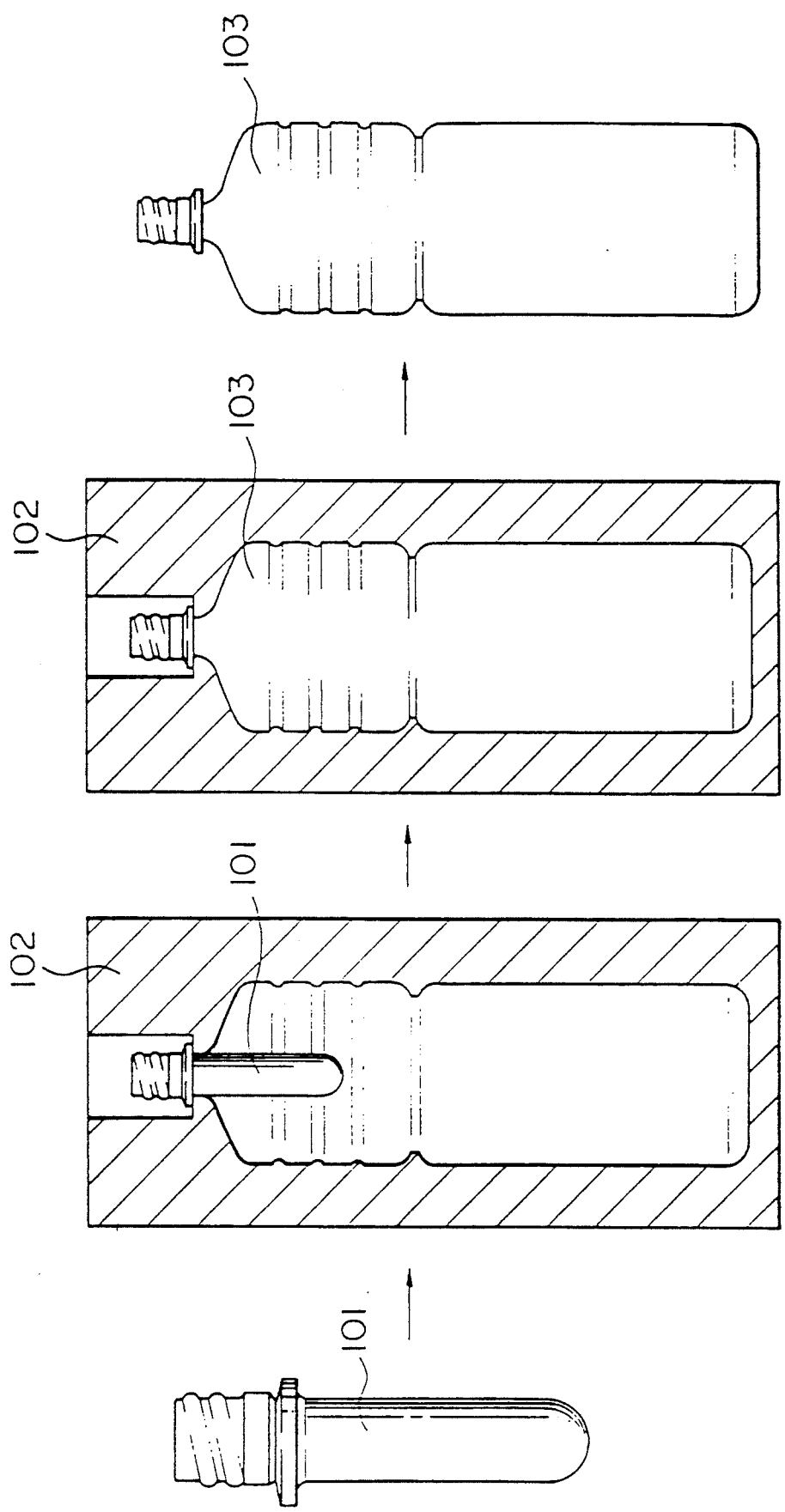
FIGS. 8(A), 8(B), 8(C) and 8(D) are views representing a manufacturing method of a container made of synthetic resin.

§1 First Embodiment of Inspection Method and Apparatus for Heat-Resistant multilayer Container made of Synthetic Resin 1.1 General Manufacturing Method of Synthetic Resin Container A general manufacturing method of a heat-resistant multilayer container made of synthetic resin is first described hereunder with reference to FIGS. 6 to 8.

At first, an injection molding machine and injection molding processes for forming a parison 101 for a blow formation due to co-injection molding are explained.

FIG. 6 is a schematic sectional side view of the injection molding machine for the co-injection molding. Referring to FIG. 6, hot runner nozzle means 104 for the co-injection molding comprises a hot-runner nozzle 105 for main resin and a hot-runner nozzle 106 for heat-resistant resin and also is provided with a hot-runner main block 107 for supporting the hot-runner nozzle means 104, a spacer block 108, a hot-runner sub-block 109 and a heat insulating plate 110. A runner 111 for the main resin is disposed in the hot-runner main block 107 and a runner 112 for the heat-resistant resin is disposed in the hot-runner sub-block 109. An injection cavity mold 113, a lip cavity mold 114 and an injection core 115 are disposed above the hot-runner nozzle means 104 for the co-injection molding.

A parison formation process carried out by arranging a mold device for the parison 101 to the co-injection molding machine of the character described above is described hereunder with reference to FIGS. 7(A), 7(B), 7(C) and 7(D).

The main resin 116 is first injected through the hot-runner nozzle 105 for the main resin into the cavity a defined by the injection cavity mold 113 and the injection core 115 (FIG. 7(A)) and the heat-resistant resin 117 is then pressure injected, with a slight time lag, into an intermediate layer of the main resin 116 in the cavity a through the hot-runner nozzle 106 for the heat-resistant resin (FIG. 7(B)). The front end portion of the heat-resistant resin 117 flows out from the front end portion of the main resin 116 near a portion at which the front end of the main resin 116 reaches a cavity b defined by the lip cavity mold 114 and the injection core 115 and the heat-resistant resin that flows out covers the front surface of the main resin 116 (FIG. 7(C)). The heat-resistant resin 117 further advances and when the portion of the heat-resistant resin 117 covering the main resin 116 reaches a closed portion of the cavity b, the heat resistant resin advances along the walls of the lip cavity mold 114 and injection core 115 (FIG. 7(D)) to thereby form a molded product, i.e. parison 101, having five-layered mouth portion and three-layered shell portion.

Next, a container forming process due to a drawing blow formation of the parison 101 is explained hereunder with reference to FIG. 8.

The parison 101 formed by the injection molding machine is first prepared (FIG. 8(A)). Next, the mouth portion of the parison 101 is grasped by a mold 102 of a drawing blow formation machine, not shown, (FIG. 8(B)) and the drawing blow formation process is carried out (FIG. 8(C)), whereby a container 103 having a predetermined shape is manufactured (FIG. 8(D)).

1.2 Basic Structure of Inspection Apparatus

Figure 1:
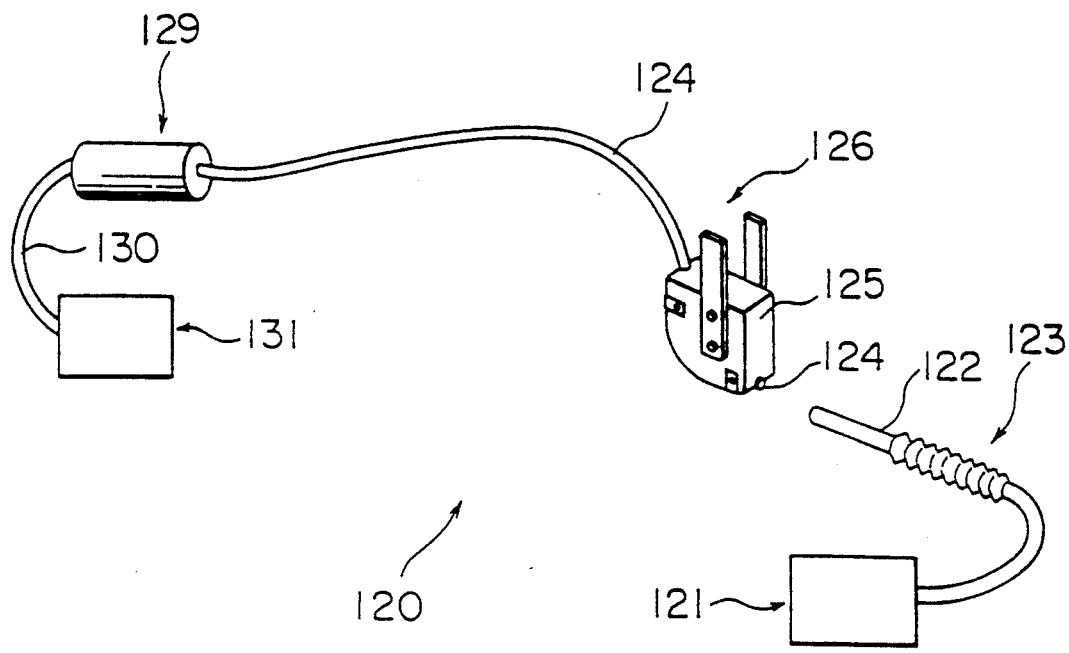
FIG. 1 is a schematic perspective view of an inspection apparatus utilized for the first embodiment of the inspection method and apparatus according to the present invention for the inspection of a heat resistant multilayer container made of synthetic resin.
Figure 2:
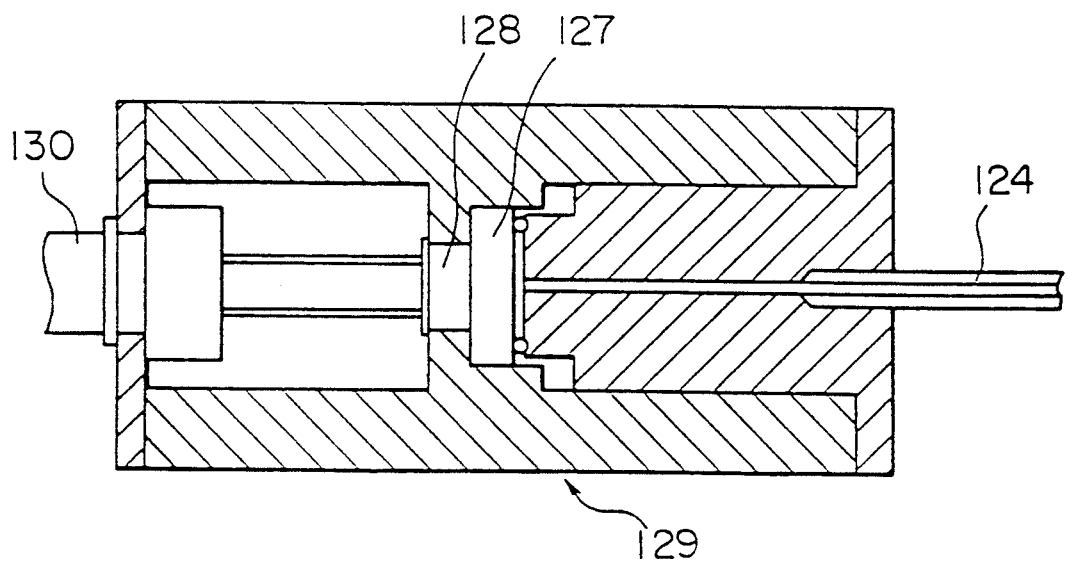
FIG. 2 is a side view of a sensor of the apparatus shown in FIG. 1.

FIG. 1 shows a schematic perspective view of an inspection apparatus and FIG. 2 shows a sectional view of the structure of a sensor.

The inspection apparatus 120 comprises a lighting device 121 provided with a mercury-xenon lamp, not shown, emitting ultraviolet rays and visual light rays, a light projecting device 123 connected to the lighting device 121 and provided with a silica series fiber 122 for lighting having a diameter of 2 mm for collecting and transferring the ultraviolet rays and visual light rays and a light receiving device 126 provided with a silica fiber 124 for detection having a diameter of 1 mm and a guide 125 for supporting the silica detecting fiber 124.

The reason for using the mercury-xenon lamp as the lighting device is for increasing the light quantity in the ultraviolet region. In addition, in the case where the positional alignment of the front ends of the silica lighting fiber 122 and the silica detecting fiber 124 is performed, visual light is emitted, and such positional alignment can be facilitated, unlike the case for ultraviolet light that cannot be observed by eye.

A sensor means 129 is disposed along the silica detecting fiber 124 and the sensor means 129 is composed of an interference filter 127 for passing only light having a specific wavelength (350 ±10 nm) and a gallium-phosphorous element 128 of photoelectric transfer type receiving the ultraviolet rays and the visual light rays. A cable 130 extending from the sensor means 129 is connected to a discriminating means 131 comprising an amplifier, not shown, and a discriminating circuit, not shown.

1.3 Inspection Method

The principle of the inspection method is first described with reference to FIG. 3. The principle is based on the property such that the main resin is superior in the transmission factor for ultraviolet light having a specific wavelength, when compared with heat-resistant resin.

Figure 3:
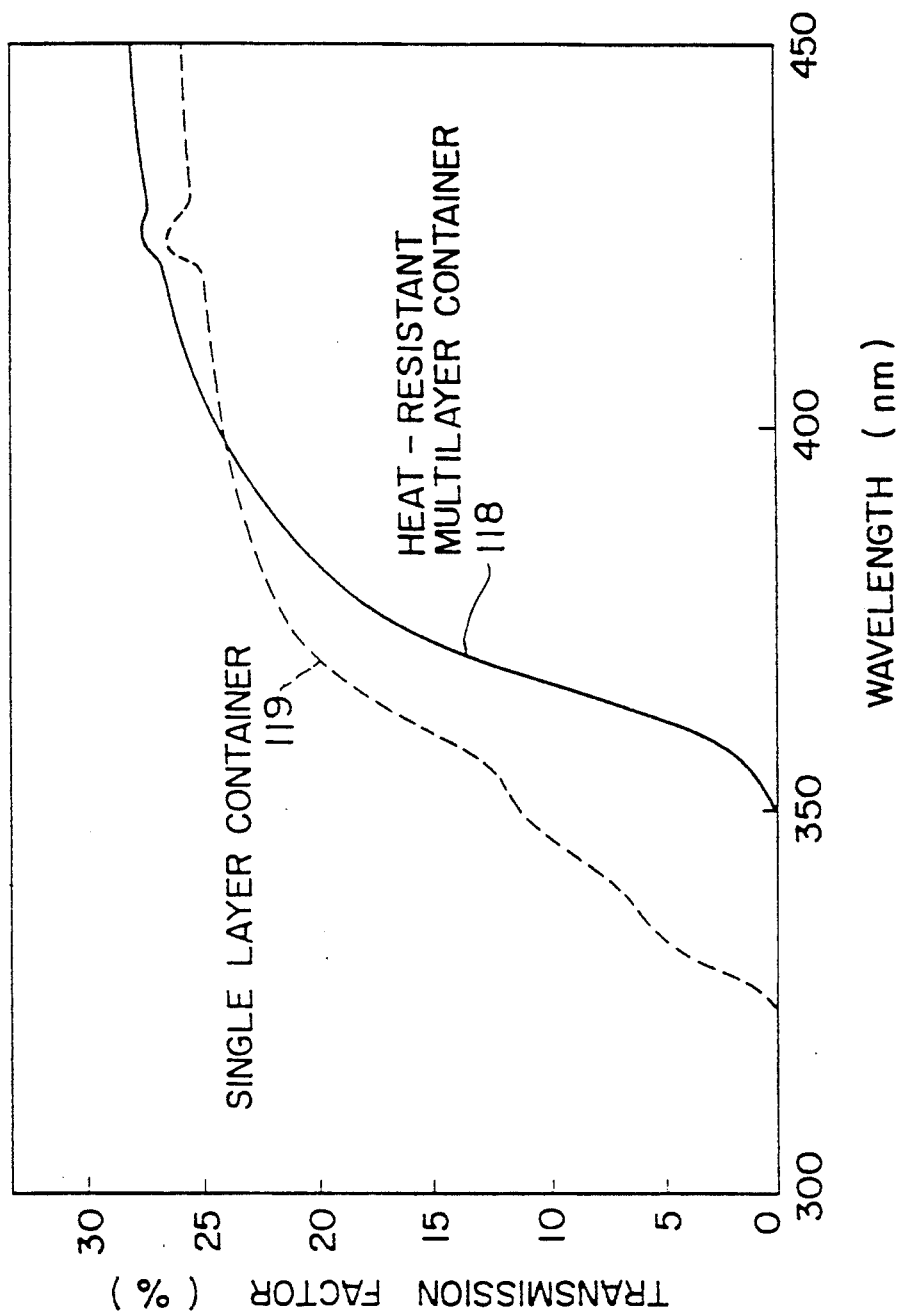
FIG. 3 is a view representing a transmission factor of a light passing a container, in accordance with the light wavelength.

FIG. 3 shows the ultraviolet ray transmission factors of the heat-resistant multilayer container 118 manufactured by the method described hereinbefore and made of a PET (polyethylene terephthalate) series resin as the main resin and a polyallylate series resin as the heat-resistant resin and a single layer container 119 manufactured by the method described hereinbefore and made of only the PET series resin.

As can be seen from FIG. 3, a remarkable difference in the transmission factors occurs near the wavelength of 350 nm.

For the PET series resin as the main resin for the heat-resistant multilayer container, there may be utilized a polyester obtained by copolymerizing a terephthalate acid or its ester formation derivative (for example, lower alkyl ester, phenyl ester) and ethylene glycol of its ester formation derivative (for example, monocarboxylic ester ethylene oxide), or by further copolymerizing an aromatic dicarboxylic acid group such as a dicarboxylic acid of less than about 20% mol, phthalic acid, isophthalic acid, naphthalene dicarboxylic acid, diphenyl dicarboxylic acid and diphenoxyethanedicarboxylic acid, or a aliphatic or alicyclic dicarboxylic acid group such as adipic acid, sebacic acid, azelaic acid, decanedicarboxylic acid, or cyclohexanedicarboxylic acid, or by copolymerizing glycol or trimethylene glycol of less than about 20% mol, an aliphatic or alicyclic glycol group such as propylene glycol, tetramethylene glycol, neopentyl glycol, hexamethylene glycol, dodecamethylene glycol or cyclohexanedimethanol, or aromatic diol group such as bisphenol group, hydroquinone, or 2-2 bis (4-β-hydroxyethoxyphenyl) propane. It may be further possible to copolymerize an oxy acid group such as P-hydroxyethoxybenzonic acid or α-oxycaproic acid, or lower alkyl ester of oxy acid or the other ester formation derivative.

A blend polymer of respectively and polyethyleneterephthalate is utilized for the respectively series resin for the heat resistant resin.

The inspection method for the heat-resistant multilayer container will be described hereunder in detail.

As can be seen from a general method of manufacturing a heat-resistant multilayer container shown in FIGS. 6 to 8, the heat-resistant resin layer flows from the lower side towards the upper side, so that it is found that the heat-resistant resin layer exists throughout the entire container in a case where the heat resistant resin layer exists to the upper end portion of the mouth portion of the container. Accordingly, the inspection method is carried out over the entire periphery of the upper end portion of the mouth portion of the container.

Generally, in many cases, the mouth portion of the container is provided with screw threads for sealing the container with a cap which is engaged with the screw thread portion and is therefore impossible to inspect the container at the screw thread portion. Accordingly, the inspection is carried out to a cylindrical portion of the upper end portion of the mouth portion provided with no screw threads (the cylindrical portion being formed for the purpose of improving a sealing effect of the container by dipping a rubber packing formed inside the cap).

Figure 4:
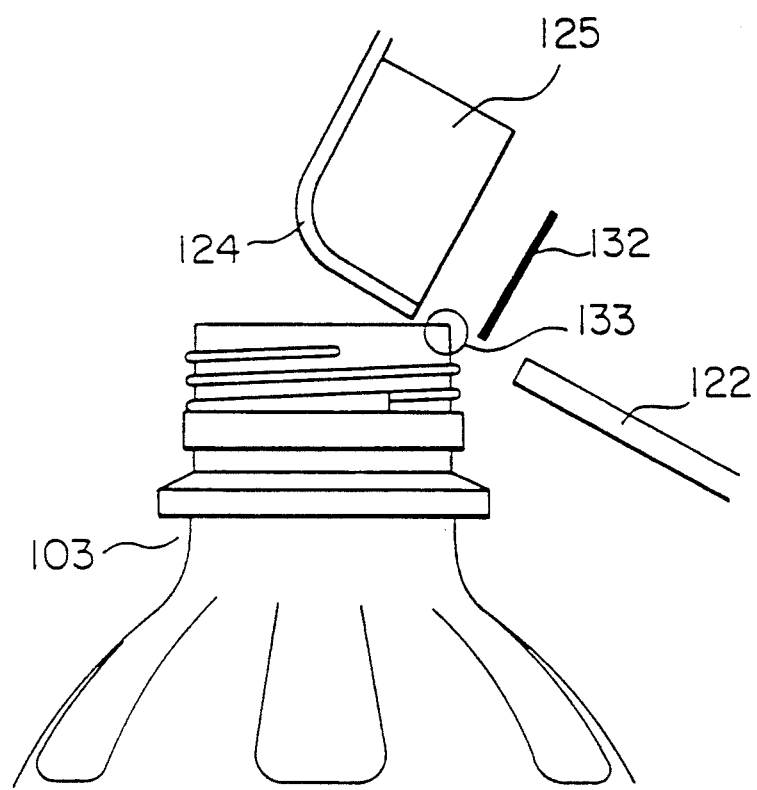
FIG. 4 is a side view explaining the inspection method by the utilization of the inspection apparatus shown in FIG. 1.

Namely, as shown in FIG. 4, the silica lighting fiber 122 and the silica detecting fiber 124 are aligned on a straight line by utilizing a visual light. Thereafter, the light emitted from the lighting device 121 is projected through the silica lighting fiber 122 and irradiated on the upper end portion 133 of the mouth portion of the container 103 with a part of the light being shielded by a shielding plate 132. The light transmitted through the upper end portion 133 of the mouth portion is received by the silica detecting fiber 124 and light having only the specific wavelength (350±10 nm) is transmitted (extracted) by the interference filter 127 of the sensor 129. At this time, when the light having the specific wavelength is detected by the gallium-phosphorous element 128, the gallium-phosphorous element 128 generates voltage, which is amplified by an amplifier and then inputted into the discrimination circuit to evaluate the quality of the container 103.

1.4 Concrete Example

The result obtained by the actual inspection by the utilization of the described inspection apparatus and method will be explained with reference to FIGS. 5(A) to 5(C).

A heat-resistant multilayer container 118 manufactured by the method described hereinbefore and made of a PET resin [MITSUI PET resin J125] as the main resin and a U polymer [UNITIKA U 8400] prepared by blending a polyallyalate and a polyethylene terephthalate as the heat-resistant resin and a single-layer container 119 made of only the PET were prepared and the inspections were performed to the entire peripheries (0° to 360°) of the upper end portions of the mouth portions of the respective containers 118 and 119.

Figure 5A:
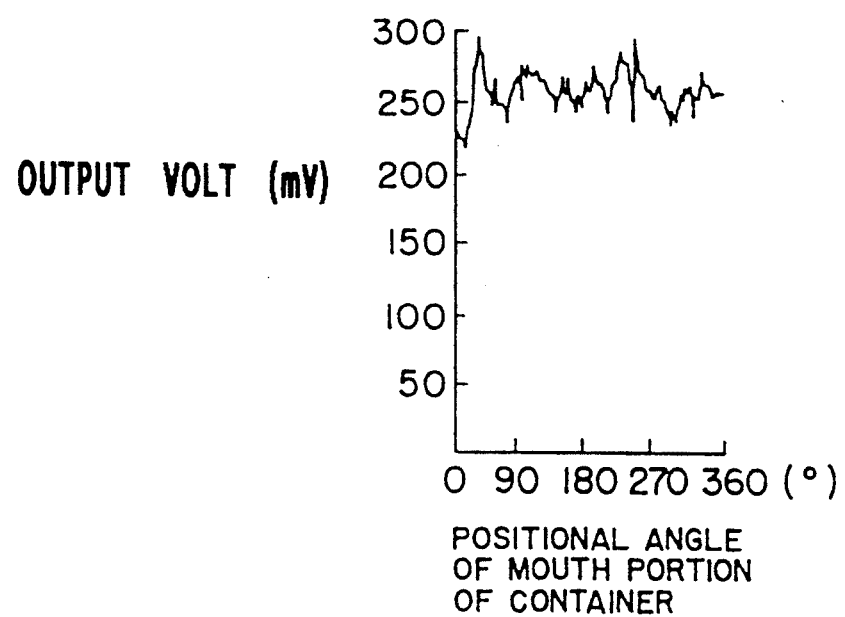
FIGS. 5(A) to (C) are views showing inspection results obtained by the inspection method of FIG. 4.
Figure 5B:
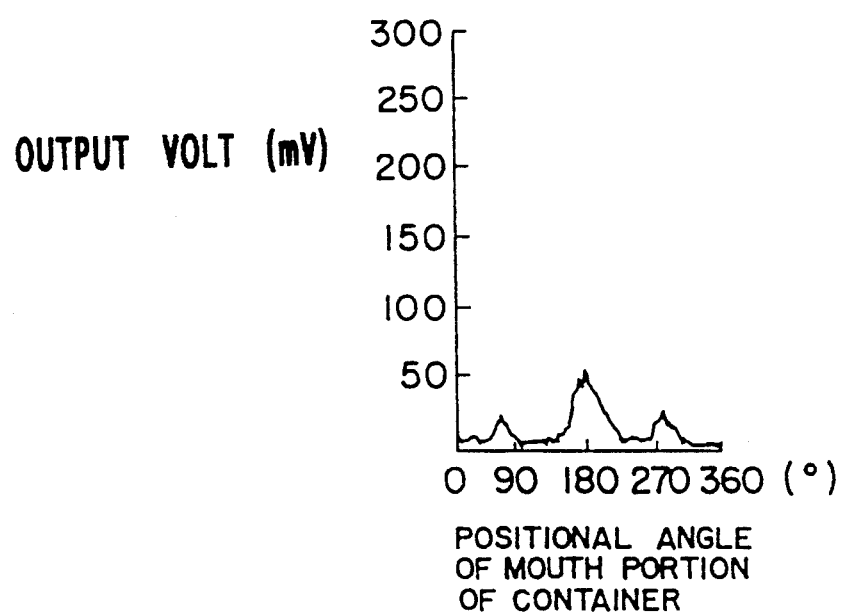
Figure 5C:
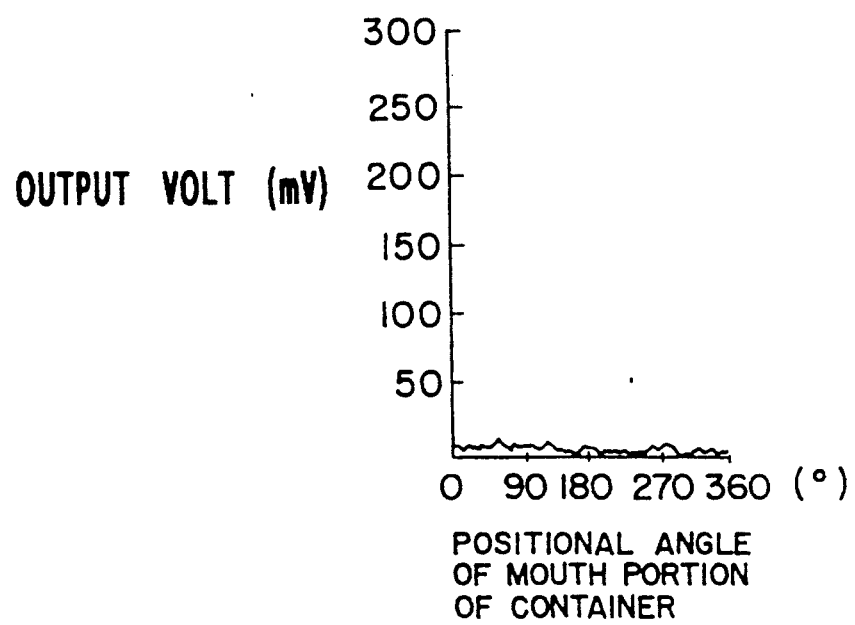

FIG. 5(A) shows the result of the single container 119 in which an output of more than 250 mV is observed throughout the entire periphery. FIG. 5(B) shows the inspection result of the heat resistant multilayer container having a fault mouth portion and an output of 25 to 50 mV is observed at positional angles near 90°, 180° and 270° of the lower screw thread portion of the mouth portion of the container. FIG. 5(C) shows the inspection result of a good heat-resistant multilayer container, in which an output is not substantially observed.

1.5 Effects

As described hereinbefore, according to the inspection apparatus and method, according to the present invention, for the synthetic resin heat resistant multilayer container, the quality of the heat resistant multilayer containers can be discriminated by detecting the transmission factors of the lights having specific wavelengths of the main resin and the heat resistant resin of the mouth portion of the container, outputting the detected result as electric voltages and evaluating the outputted value. Namely, it can be determined whether or not the heat-resistant resin layer exists throughout the entire heat resistant multilayer container. As described, definite inspection can be performed in a short time, so that the number of inspection processes can be eliminated and products of high quality can be produced.

§2 Second Embodiment of Inspection Method and Apparatus of Heat-Resistant Multilayer Container made of Synthetic Resin

2.1 Basic Structure of Inspection Apparatus

Figure 9:
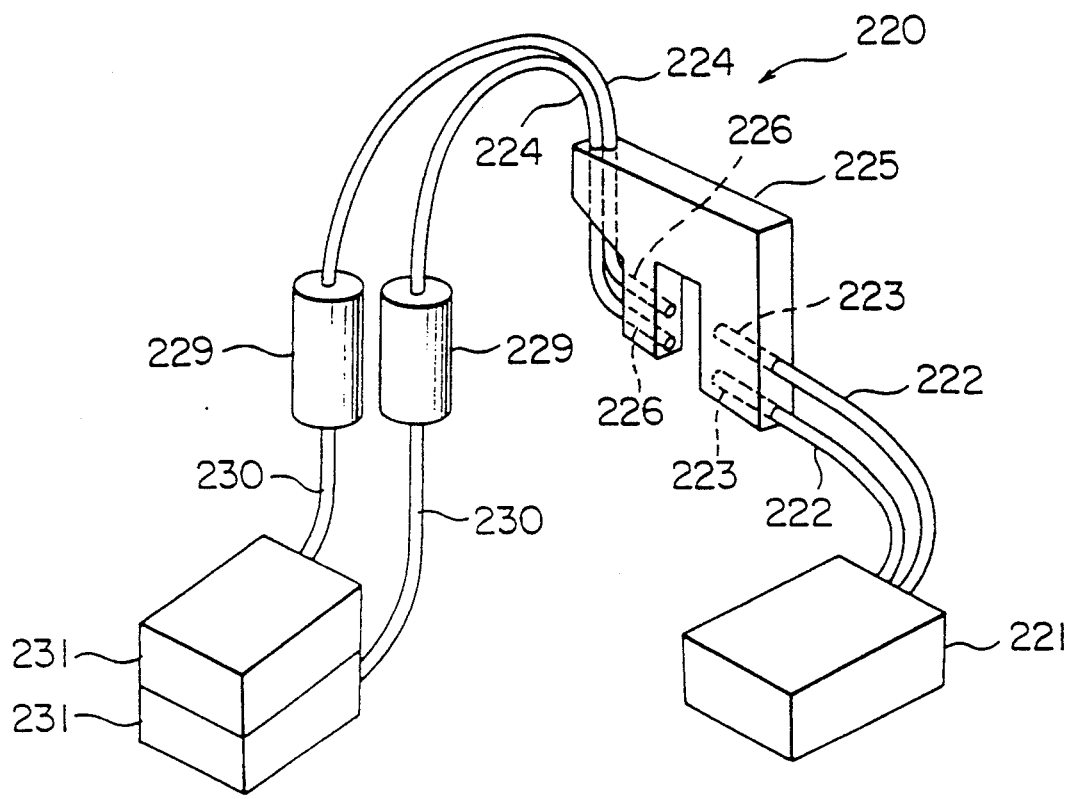
FIG. 9 is a schematic perspective view of an inspection apparatus utilized for the second embodiment of inspection method and apparatus according to the present invention for the inspection of a heat resistant multilayer container made of synthetic resin.
Figure 10:
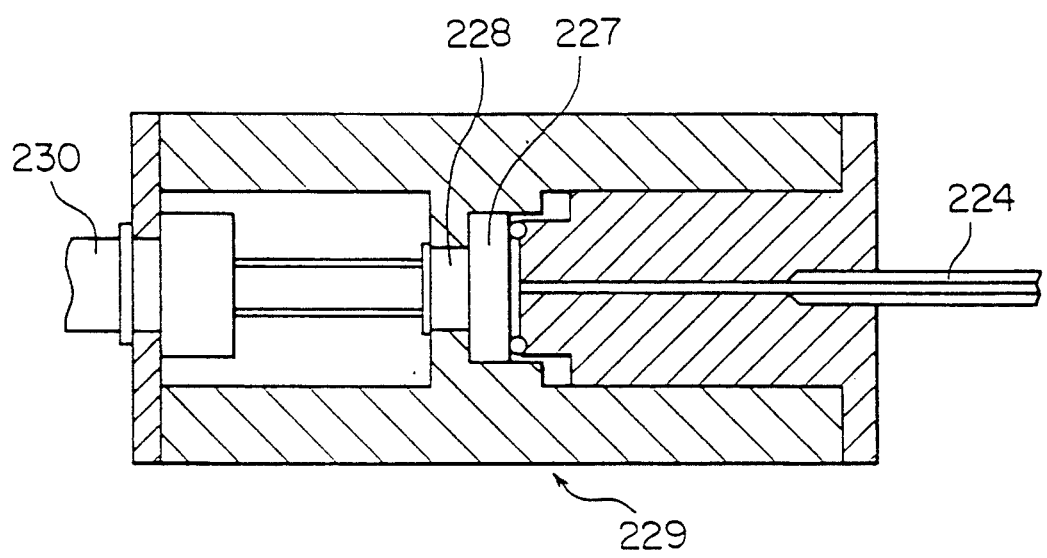
FIG. 10 is a side view of a sensor of the apparatus shown in FIG. 9.

FIG. 9 is a perspective view showing a schematic structure of the inspection apparatus and FIG. 10 is a sectional side view showing a structure of a sensor means.

The inspection device 220 covers the ultraviolet emission area and comprises a lighting device 221 provided with, for example, a mercury-xenon lamp, not shown, which emits ultraviolet rays and visible light rays, two silica fibers 222 and 222 for lighting connected to the lighting device 221, each having a diameter of 2 mm so as to collect and transfer the ultraviolet rays and the visible light, and two silica fibers 224 and 224 for detection, each having a diameter of 1 mm to receive the light projected. The two silica lighting fibers 222 and 222 have front ends 223 and 223 which are supported by a guide 225 to be parallel in vertical arrangement so that the distance therebetween is equal to the distance between the upper end portion of the mouth portion of the container and the lower screw thread portion. The silica detecting fibers 224 and 224 have front ends 226 and 226 which are supported by the guide 225 so that the front ends 226 and 226 are opposed to the front ends 223 and 223 with predetermined spaces therebetween.

The reason for using mercury-xenon lamp as lighting device is for increasing the light quantity in the ultraviolet region. Sensor means 229 are disposed on the way of the respective silica detecting fibers 224 and 224. Each of the sensor means 229 comprises an interference filter 227 for passing only the specific wavelength (350±10 nm) and a gallium-phosphorous element 228 for receiving the ultraviolet rays and the visual light rays. Cables 230 and 230 extending from the respective sensor means 229 and 229 is connected to discriminating means 231 and 231 each composed of an amplifier, not shown, and a discrimination circuit, not shown.

2.2 Inspection Method

As described in connection with the inspection method of 1.3 described hereinbefore, the fact that the heat-resistant resin layer exists at the upper end portion of the mouth portion of the container, means that the heat-resistant resin layer exists entirely to the container, so that the quality of the heat-resistant multilayer container can be discriminated by inspecting the entire periphery of the upper end portion of the mouth portion of the container. Furthermore, the flow condition of the heat-resistant resin layer can be evaluated by inspecting the entire periphery of the lower screw thread portion of the mouth portion. Accordingly, according to this embodiment, a cylindrical portion directly below the screw thread portion is inspected in addition to the inspection of a cylindrical portion of the upper end portion of the mouth portion including no screw thread portion.

Figure 11:
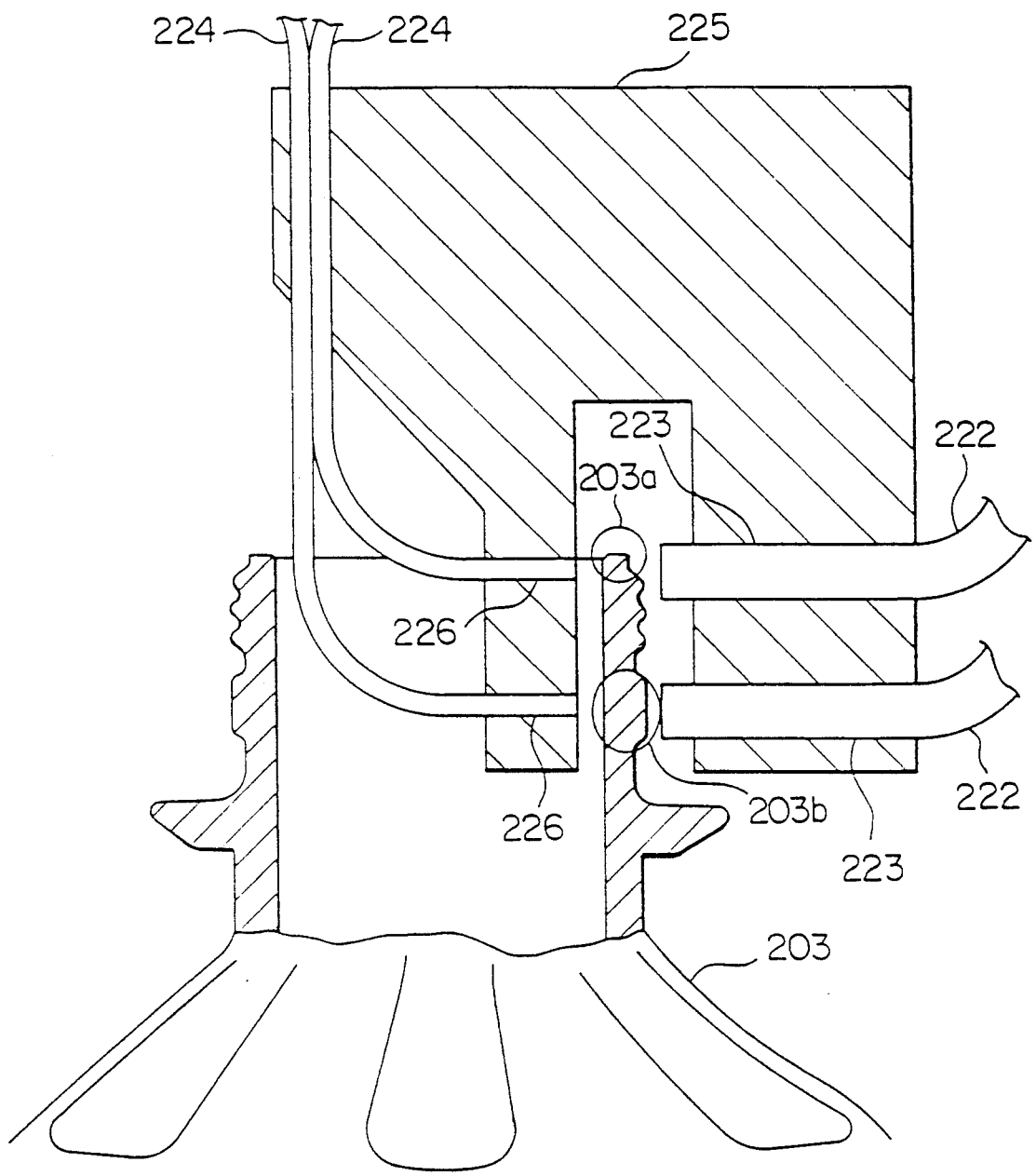
FIG. 11 is a side view explaining the inspection method by the utilization of the inspection apparatus shown in FIG. 9.

Namely, as shown in FIG. 11, the front ends 223 and 223 of the respective two silica lighting fibers 222 and 222 and the front ends 226 and 226 of the respective two silica detecting fibers 224 and 224 are arranged so as to respectively hold the upper end portion of the mouth portion of the container and the lower screw thread portion of the mouth portion. Thereafter, the lights emitted from the lighting devices 221 are projected through the two silica series lighting fibers 222 and 222 and irradiated on the upper end portion 203a of the mouth portion of the container and the lower screw thread portion 203b of the mouth portion. The lights passing the upper end portion 203a and the lower screw thread portion 203b of the mouth portion are received by the two silica series detecting fibers 224 and 224 and the lights having only the specific wavelengths (350±10 nm) pass (are extracted) by the interference filters 227 and 227 disposed in the sensor means 229 and 229. When the lights having the specific wavelengths are detected by the gallium-phosphorous elements 228 and 228, the gallium-phosphorous elements 228 and 228 generate electric currents, which are then amplified by the amplifiers and input into the discrimination circuits, respectively, to evaluate the quality of the container 203.

Namely, as is similar to the inspection method of 1.3 described hereinbefore, it is determined whether or not the heat resistant resin layer exists throughout the container by inspecting the entire periphery of the upper end portion 203a of the mouth portion of the container. As shown in FIGS. 7(A), 7(B), 7(C) and 7(D) during the parison 101 formation process, the heat-resistant resin 117 flows along the wall surfaces of the lip cavity mold 114 and the injection core 115 to form the mouth portion having a five-layered structure and such flow condition can be discriminated by inspecting the entire periphery of the lower screw thread portion 203b of the mouth portion.

2.3 Concrete Example

Figures 1, 12A:
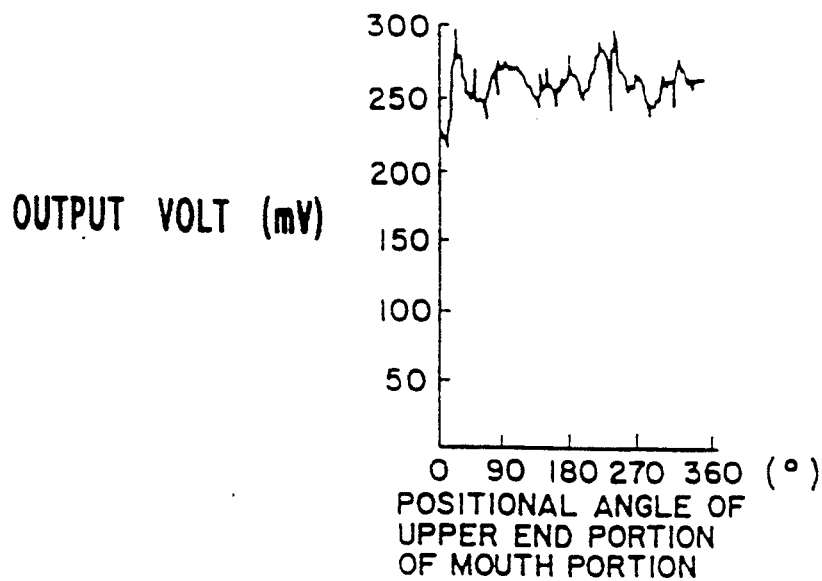
FIGS. 12(A), 12(B) and 12(C) are views showing inspection results obtained by the inspection method of FIG. 11.
Figures 2, 12A:
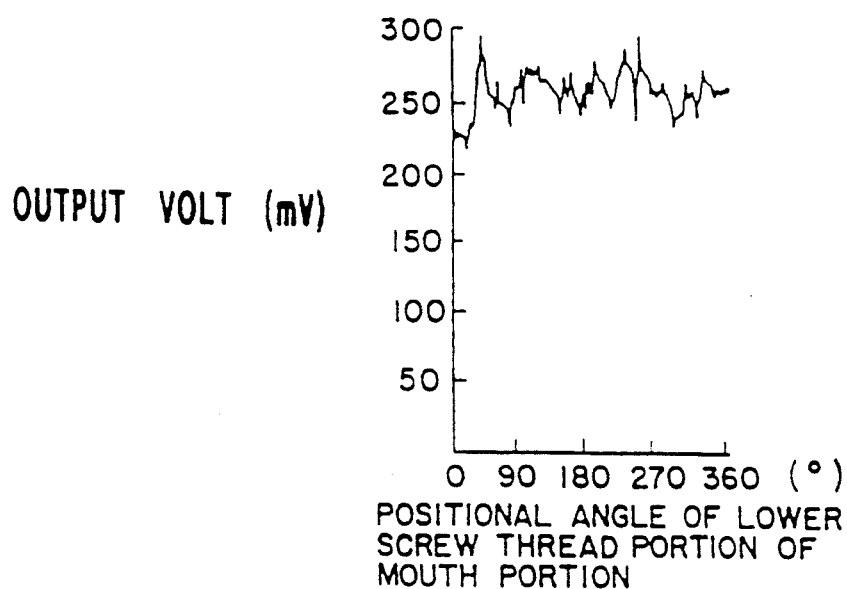
Figures 1, 12B:
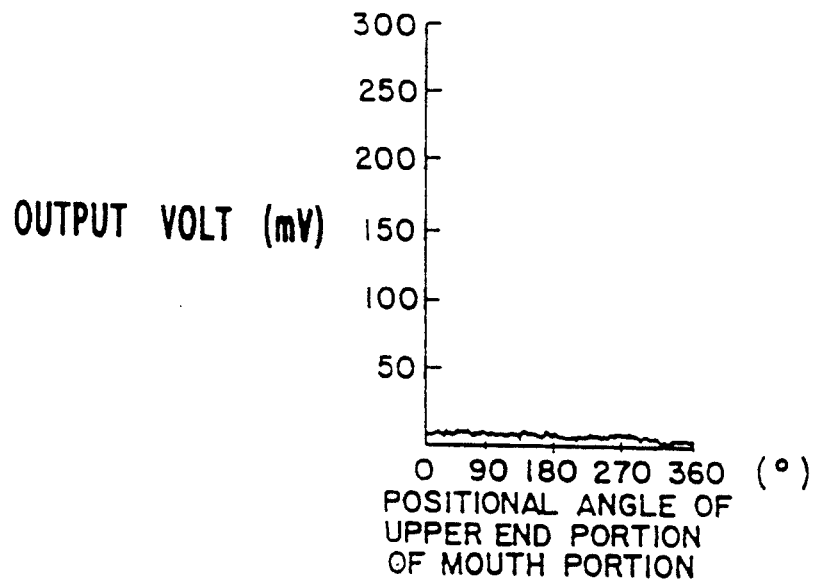
Figures 2, 12B:
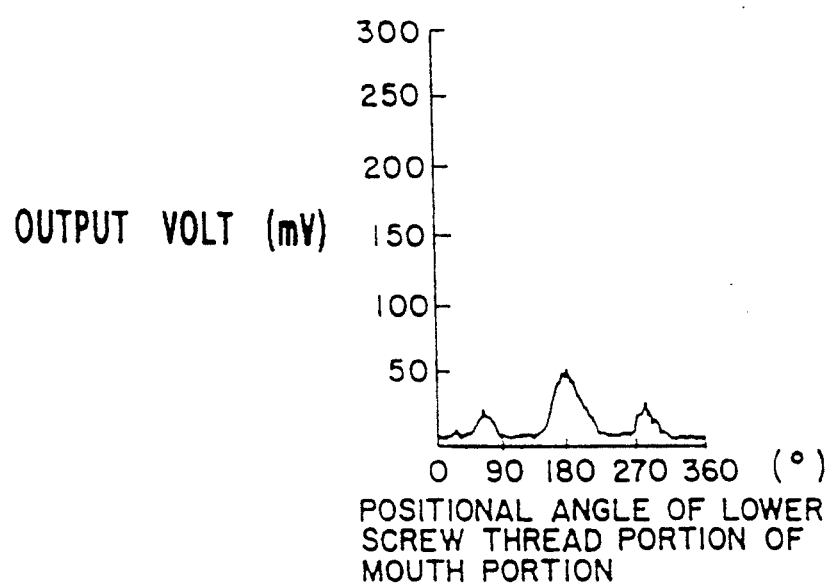
Figures 1, 12C:
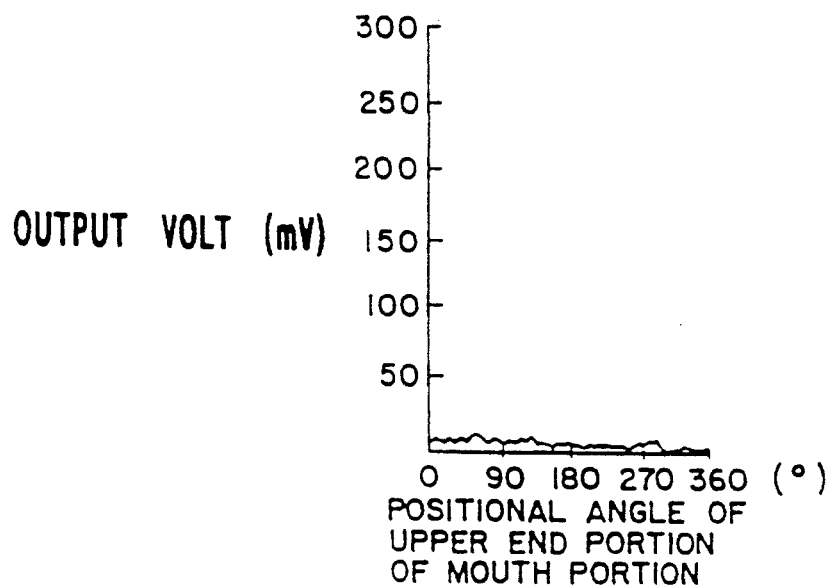
Figures 2, 12C:
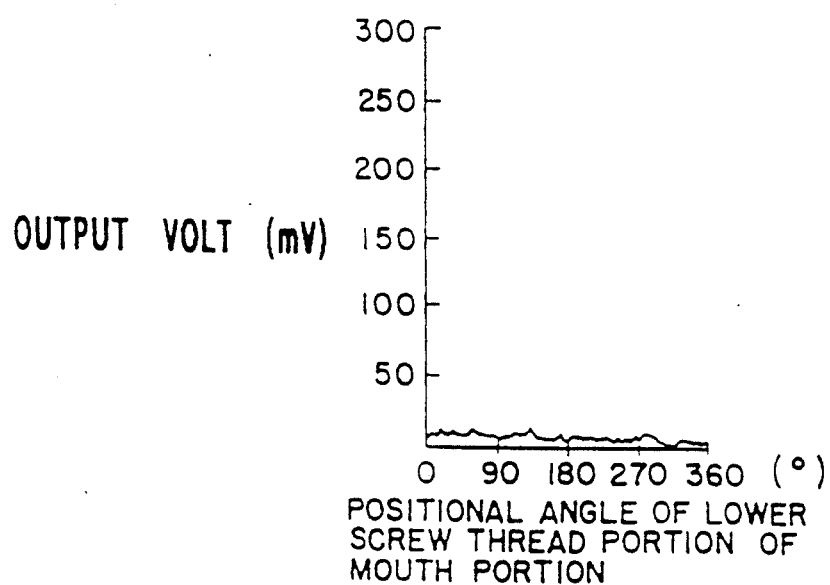

Actual inspection results of the upper end portion and the lower screw thread portion of the mouth portion of the container performed by the inspection apparatus and inspection method described above are explained hereunder with reference to FIGS. 12(A), 12(B) and 12(C).

A heat resistant multilayer container 118 manufactured by the method described hereinbefore and made of a PET resin [MITSUI PET resin J125] as the main resin and a U polymer [UNITIKA U 8400] prepared by blending a polyallyrate and a polyethylene terephthalate as the heat-resistant resin and a single layer container 119 made of only the PET were prepared. The inspections were performed to the entire peripheries (0° to 360°) of the upper end portions of the mouth portions and the lower screw thread portions of the mouth portions of the respective containers 118 and 119. FIG. 12(A) shows the result of the single container 119 in which an output of more than 250 mV is observed throughout the entire periphery. FIG. 12(B) shows the inspection result of the heat-resistant multilayer container having a fault mouth portion and an output of 25 to 50 mV is observed at positional angles near 90°, 180° and 270° of the lower screw thread portion of the mouth portion of the container. FIG. 12(C) shows the inspection result of the good heat-resistant multilayer container, in which an output is not substantially observed.

2.4 Effects

As described hereinbefore, according to the inspection apparatus and method, according to the present invention, for the synthetic resin heat-resistant multilayer container, the quality of the heat-resistant multilayer containers can be evaluated by detecting the transmission factors of the lights having specific wavelengths of the main resin and the heat-resistant resin of the upper end portion and the lower screw thread portion of the mouth portion of the container, outputting the detected result as electric voltages and evaluating the outputted value. Namely, it can be determined whether or not the heat-resistant resin layer exists throughout the entire heat-resistant multilayer container and whether or not the heat-resistant resin layer surely flows in the mouth portion to form an ideal mouth portion.

Figure 13A:
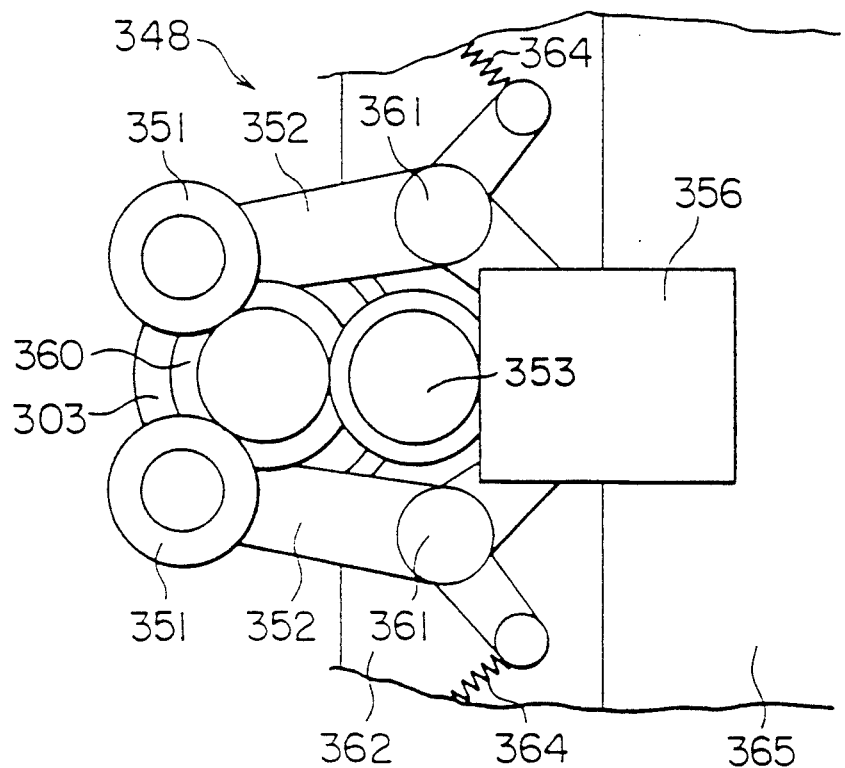
FIGS. 13(A) and (B) are plan and side views showing an embodiment of a container rotating mechanism according to the present invention.
Figure 13B:
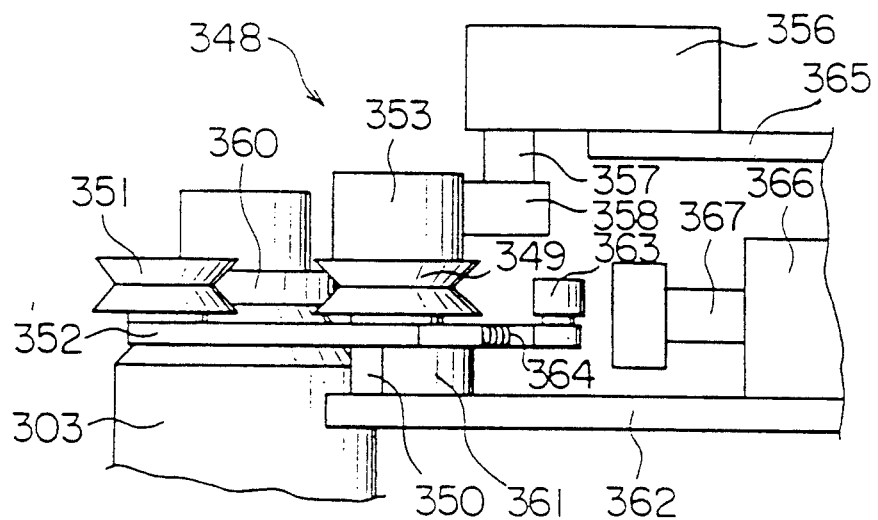

§3 Embodiments of Container Rotating Mechanism and Container Transfer Device for Inspection of Container 3.1 Container Rotating Mechanism FIG. 13(A) is a plan view showing a main part of the container rotating mechanism and FIG. 13(B) is a side view thereof.

A container supporting mechanism 348 comprises a shaft 350 provided with a driving roller 349 for rotating a container 303 and a pair of roller support rods 352 provided with rotatable rollers. A rotating shaft 361 of each of the roller support rods 352 is mounted on a table 362 so that the paired roller support rods 352 and 352 snap the shaft 350. As described, three rollers 349, 351 and 351 are arranged in a triangle form. A rotating gear 353 is secured to the upper portion of the driving roller 349 and the rotating gear 353 is meshed with a driving gear 358 connected to an output shaft 357 of an electric motor 356 mounted on a table 365 disposed to the upper portion of the table 362. Each of the roller supporting rods 352 has a Y-shape with the rotating shaft 361 being the center thereof and the rotatable roller 351, an opening-closing roller 363 and one end of a spring 364 are secured to the respective end portions of the Y-shaped roller support rod 352. An air cylinder 366 and a core rod 367 are secured on the table 362 disposed rearward of the opening-closing roller 363.

The operation of this embodiment will be described hereunder.

The core rod 367 is moved leftwardly as viewed in FIG. 13(B) in response to the operation of the air cylinder 366 to push the paired rollers 363 and 363 and to bilaterally expand the paired support rods 352 and 352 with the roller rotating shaft 361 being the center of the rollers 363 and 363. When the flanged portion 360 of the mouth portion of the container 303 is intruded into the space between the paired roller support rods 352 and 352, the air cylinder 366 again operates to move the core rod 367 rightwardly as viewed in FIG. 13(B). In such case, the spring 364 returns to the original position to thereby close the paired roller support rods 352 and 352 with the roller rotating shaft 361 being the center thereof and to hold the flanged portion 360 of the mouth portion of the container 303 with neck-in portions of the three rollers 349, 351 and 351. In the next step, when the motor 356 is driven, the driving roller 349 is rotated through the output shaft 357, the driving gear 358 and the driving gear 353. The container 303 and the paired rotatable rollers 351 and 351 are rotated by the friction force caused by the rotation of the driving roller.

Since these rotations are carried out by supporting the upper end portion of the container 303 at three portions, the container 303 can be surely held and rotated while maintaining the stable rotating condition in the perpendicular attitude.

The transfer of this rotation may be carried out by suitable means not limited and carried out by a belt in substitution for the gear, a hydraulic cylinder in substitution for the air cylinder 366 and an air cylinder in substitution for the spring 364.

3.2 Container Transfer Device

Figure 14A:
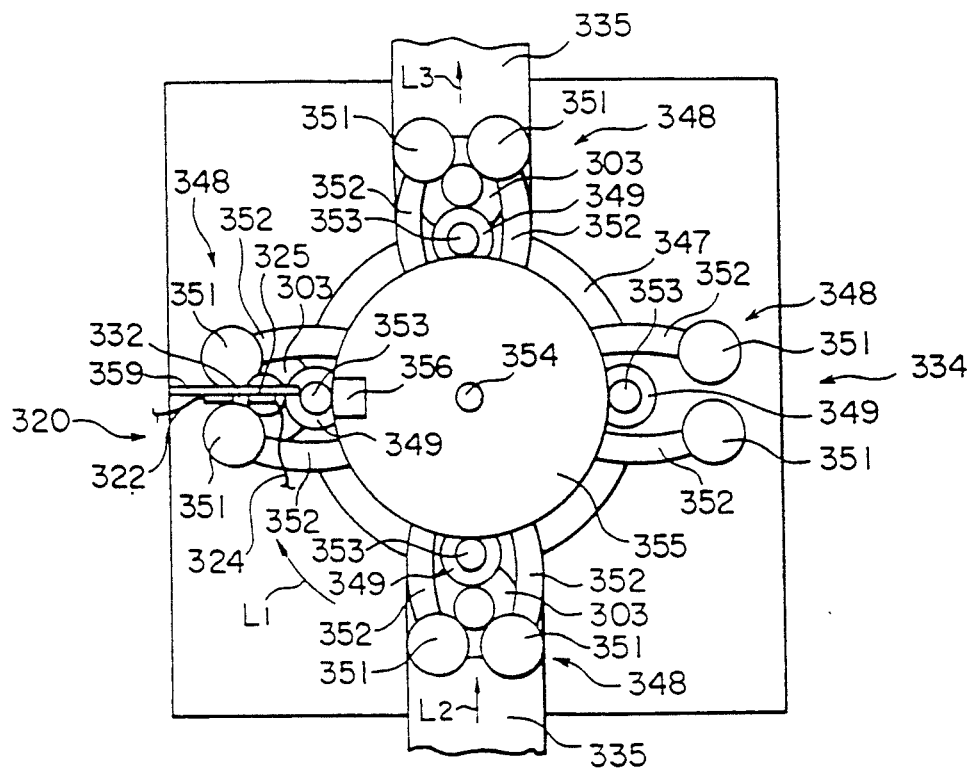
FIGS. 14(A) and (B) are plan and side views showing an embodiment of a container transfer device according to the present invention.
Figure 14B:
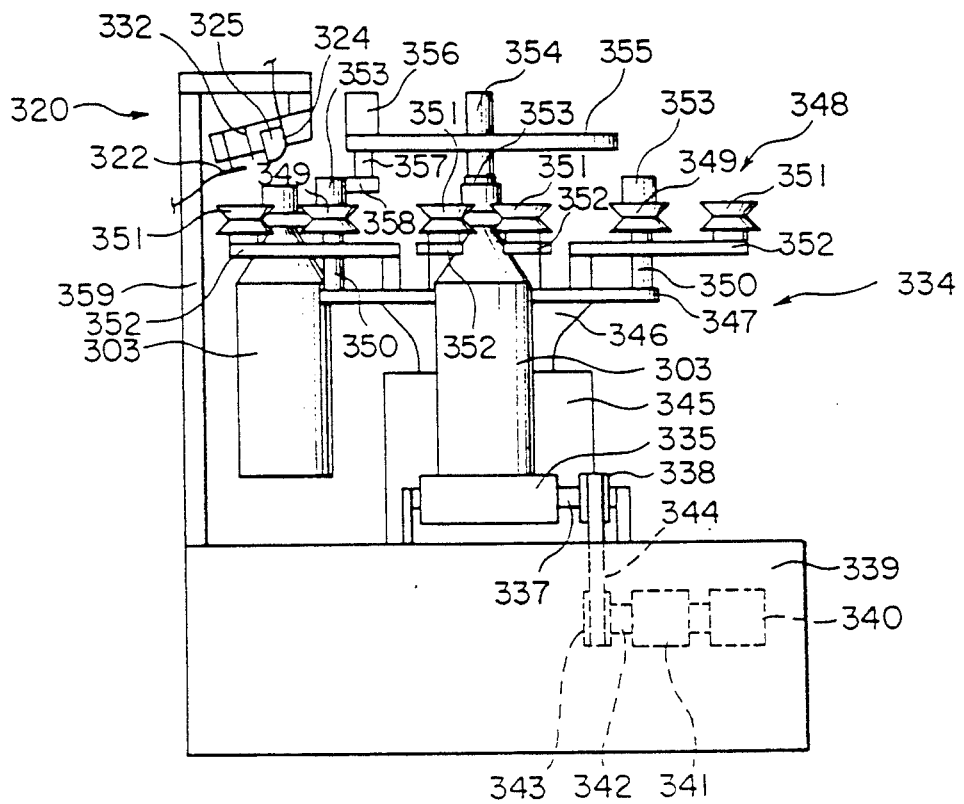

FIG. 14(A) is a plan view showing a schematic structure of the container transfer device provided with the container rotating mechanism 348 of the character described above and FIG. 14(B) is a side view thereof.

The container transfer device 334 comprises two conveyer belts 335 and 335 and a rotary disc 347 disposed between these conveyer belts 335 and 335. Rollers for the conveyer belts, not shown, are arranged to the rear end portions of the conveyer belts 335 and 335. Pulleys 338 and 338 mounted to the end portions of roller shafts 337 and 337 for the conveyer belts are connected through a belt 344 to a pulley 343 mounted on the output shaft 342 of a reduction mechanism 341 of the motor 340 disposed in the main body 339, whereby the conveyer belts 335 and 335 are driven.

The rotary disc 347 is rotated in a state that the rotary disc 347 is secured to the rotating shaft 346 rotated by a container rotating mechanism 345. The container rotating mechanism 345 is disposed to the upper portion of the main body 339. Four container rotating mechanisms 348, 348, 348 and 348 are arranged with spaces apart by 90° with each other along the circumferential portion of the rotary disc 347, each container rotating mechanism 348 comprising a shaft 350 on which a driving roller 349 is mounted and a pair of roller support rods 352 and 352 provided with rotatable rollers 351 and 351. The three rollers 349, 351 and 351 are arranged in a triangle form and the rotating gear 353 is secured to the upper portion of the driving roller 349 arranged inside. Furthermore, a shaft 354 now stopped without being influenced by the rotation of the rotating shaft 346 is disposed to the upper portion of the rotary disc 347 and a stopping disc 355 is secured to the shaft 354. A motor 356 is mounted to the circumferential portion of the stopping disc 355 leftwardly apart by 90° in a rotating direction of the conveyer (arrowed direction $L_1$ in FIG. 14(A) providing that the conveying direction of the conveyer belt 335 has an angle of 0°) and the output shaft 357 of the motor 356 is positioned so that the driving gear 358 mounted to the end portion of the output shaft 357 is meshed with the rotating gear 353. In a similar manner, an inspection apparatus 320 having substantially the same structure as that of the inspection apparatus (FIG. 1) of the first embodiment is arranged at a portion further leftwardly apart by 90° from the motor 356.

The inspection apparatus 320 is composed of a silica lighting fiber 332 secured to the front end of an L-shaped sensor support rod 359 suspended from the upper portion of the main body 339, a silica detecting fiber 324 having a guide 325 secured to the front end of the sensor support rod 359, and a light shielding plate 332.

The operation of the embodiment described above will be described hereunder.

The container 303 is rested on the conveyer belt 335 and the motor 340 is driven to rotate the driving roller, not shown, to move the container 303 in an arrowed direction $L_2$ shown in FIG. 14(A). The roller support rods 352 and 352 of the container rotating mechanism 348 are bilaterally opened to receive the container 303 therebetween and the flanged portion 360 of the mouth portion of the container is held by the three rollers 349, 351 and 351. In this state, the container 303 is rotated together with the rotary disc 347 in the arrowed direction $L_1$ in FIG. 14(A). In accordance with this operation, the rotating gear 353 comes into engagement with the driving gear 358 and the rotary disc 347 stops.

In the subsequent operation, the inspection apparatus 320 lowers along the sensor support rod 359 to the predetermined position of the upper portion of the mouth portion of the container 303 and the motor 356 is driven. The rotation of the motor is transmitted to the driving roller 349 through the driving gear 358 and the rotating gear 353 and the container 303 and the rotatable two rollers 351 and 351 are accordingly rotated by the friction force of the driving roller. These rotations are carried out while supporting the upper portion of the container 303 at three portions, so that the container 303 can be accurately maintained in the perpendicular attitude and the rotation thereof can be stably done.

In accordance with the operations of the respective members described above, the inspection apparatus 320 can perform the inspection, as described hereinbefore, the entire periphery of the mouth portion of the container 303. After the completion of the inspection, the inspection apparatus 320 moves upwardly along the sensor support rod 359 and the container 303 is again rotated together with the rotary disc 347 by 90° in the arrowed direction. Next, the roller support rods 352 and 352 are separated to be opened bilaterally to release the container 303, which is then mounted on the conveyer belt 335 and moved in a direction $L_3$ indicated by the arrow in FIG. 14(A). Although the above operations were described with respect to one container, these operations are repeatedly carried out in a case where containers are continuously conveyed.

In the described embodiment, the inspection apparatus 320 only for inspecting the upper end portion of the mouth portion of the container is arranged to the transfer device 334, the inspection apparatus (refer to FIG. 9) for inspecting the upper end portion and the lower screw thread portion of the mouth portion may be arranged to the transfer device without being limited to the described embodiment.

In addition, a foreign material inspection apparatus for the container may be arranged in addition to the inspection apparatus 320 to the container transfer device 334.

3.3 Effects

As described hereinbefore, according to the container rotating mechanism, the upper portion of the container is supported at three portions, so that the container can be accurately held and the accurate inspection throughout the entire periphery of the container can be performed by stably rotating the container while maintaining an exact perpendicular attitude. Moreover, according to the container transfer device provided with the described container rotating mechanism, a plurality of containers can be continuously transferred, thus continuously inspecting a plurality of containers.

I claim:

1. A method of inspecting a heat resistant multilayer container made of synthetic resin characterized by projecting light to an upper end portion of a mouth portion of a heat resistant multilayer container formed by blow forming a parison made of a main resin and heat-resistant resin, receiving light passing the upper end portion of the mouth portion, extracting and detecting light having a specific wavelength, outputting the light as an electrical signal and evaluating the quality of the heat resistant multilayer container in accordance with the outputted signal value.

2. A method of inspecting a heat-resistant multilayer container made of synthetic resin characterized by projecting light to an upper end portion of a mouth portion and a lower thread portion of the mouth portion of a heat-resistant multilayer container formed by blow forming a parison made of main resin and heat resistant resin, receiving light passing the upper end portion and the lower screw thread portion of the mouth portion, extracting and detecting a light having a specific wavelength, outputting the light as an electrical signal and evaluating the quality of the heat-resistant multilayer container in accordance with the output signal value.

3. A method of inspecting a heat-resistant multilayer container made of synthetic resin according to claim 1, wherein the heat-resistant resin is a polyallylate series resin.

4. A method of inspecting a heat-resistant multilayer container made of synthetic resin according to claim 1, wherein the light is ultraviolet.

5. A method of inspecting a heat-resistant multilayer container made of synthetic resin according to claim 3, wherein the specific wavelength to be extracted is in the range of 350±10 nm.

6. A method of inspecting a heat-resistant multilayer container made of synthetic resin according to claim 2, wherein the heat-resistant resin is a pollyallylate series resin.

7. A method of inspecting a heat-resistant multilayer container made of synthetic resin according to claim 6, wherein the specific wavelength to be extracted is in the range of 350±10 nm.

8. A method of inspecting a heat-resistant multilayer container made of synthetic resin according to claim 2, wherein the light is ultraviolet.

9. An apparatus for inspecting a heat-resistant multilayer container made of synthetic resin, comprising a lighting device for emitting light, a light projecting device connected to the lighting device for transferring and projecting the light to an upper end portion of a mouth portion of a heat-resistant multilayer container made of synthetic resin, a light receiving device located opposingly to the light projecting device for receiving and transferring the light passing through the upper end portion of the mouth portion of the container, a sensor for extracting and detecting a light transmitted from the light receiving device, and a signal processing circuit means for processing an electrical signal from the sensor to provide an indication of the condition of the heat-resistant multilayer container made of synthetic resin.

10. An apparatus for inspecting a heat-resistant multilayer container made of synthetic resin, comprising a lighting device for emitting light, a plurality of light projecting devices each connected to the lighting device for transferring and projecting the light to an upper end portion and a lower screw thread portion of a mouth portion of a heat-resistant multilayer container made of synthetic resin, a plurality of light receiving devices located opposingly to the light projecting device for receiving and transferring the light passing through the upper end portion and the lower screw thread portion of the mouth portion of the container, a plurality of sensors for extracting and detecting lights transmitted from the respective light receiving devices, and a plurality of signal processing circuit means for processing electric signals from the respective sensors to provide an indication of the condition of the heat-resistant multilayer container made of synthetic resin.

11. An apparatus for inspecting a heat-resistant multilayer container made of synthetic resin according to claim 9, wherein the light projecting device is a light projecting fiber.

12. An apparatus for inspecting a heat-resistant multilayer container made of synthetic resin according to claim 9, wherein the light receiving device is a light receiving fiber.

13. An apparatus for inspecting a heat-resistant multilayer container made of synthetic resin according to claim 10, wherein the light projecting devices are light projecting fibers.

14. An apparatus for inspecting a heat-resistant multilayer container made of synthetic resin according to claim 10, wherein the light receiving devices are light receiving fibers.

* * * * *